United States Patent [19]

Fischer et al.

[11] Patent Number: 5,798,376
[45] Date of Patent: Aug. 25, 1998

[54] AZATRIOXASPIROALKENES AND THEIR USE AS INSECTICIDAL, ACARICIDAL AND NEMATOCIDAL AGENTS

[75] Inventors: Reiner Fischer, Monheim; Ulrike Wachendorff-Neumann, Neuwied; Christoph Erdelen, Leichlingen; Andreas Turberg, Erkrath; Norbert Mencke, Leverkusen, all of Germany

[73] Assignee: Bayer Aktiengesellschaft, Leverkusen, Germany

[21] Appl. No.: 676,155

[22] PCT Filed: Jan. 4, 1995

[86] PCT No.: PCT/EP95/00023

§ 371 Date: Jul. 11, 1996

§ 102(e) Date: Jul. 11, 1996

[87] PCT Pub. No.: WO95/19364

PCT Pub. Date: Jul. 20, 1995

[30]  Foreign Application Priority Data

Jan. 17, 1994 [DE] Germany ............... 44 01 105.9
Sep. 2, 1994 [DE] Germany ............... 44 31 225.3

[51] Int. Cl.$^6$ ............................................. C07D 498/10
[52] U.S. Cl. ............ 514/374; 548/216; 546/271.4; 514/340; 549/330
[58] Field of Search ............................. 514/374; 548/216

[56]  References Cited

U.S. PATENT DOCUMENTS

| | | |
|---|---|---|
| 3,901,906 | 8/1975 | Kozlik ............... 548/239 |
| 4,216,162 | 8/1980 | Arut ............... 514/374 |
| 4,253,978 | 3/1981 | Gemmiu ............... 548/21.6 |
| 5,444,079 | 8/1995 | Amoo ............... 514/374 |

OTHER PUBLICATIONS

Mencke et al. Chem Abst. vol. 126 Entry 101492, 1997.

Harda. Chem. Abstr. vol. 125 Entry 317321, 1996.

Reisch et al. Chem Abstr vol. 116 Entry 235579, 1992.

Reisch et al Chem. Abstr. vol. 112 Entry 178869, 1990.

*Primary Examiner*—Donald G. Daus
*Attorney, Agent, or Firm*—Sprung Kramer Schaefer & Briscoe

[57]  ABSTRACT

The invention relates to new azatrioxaspiroalkenes of the formula (I)

$$\text{Ar}^1 \text{...} \text{N} \text{...} \text{O} \text{...} \text{Ar}^2 \quad (I)$$

in which $Ar^1$ and $Ar^2$ are identical or different and independently of one another in each case represent optionally substituted aryl, to processes for their preparation, to new intermediates, and to the use of the azatrioxaspiroalkenes of the formula (I) as pesticides.

3 Claims, No Drawings

AZATRIOXASPIROALKENES AND THEIR USE AS INSECTICIDAL, ACARICIDAL AND NEMATOCIDAL AGENTS

The invention relates to new azatrioxaspiroalkenes, to a plurality of processes for their preparation, and to their use for combating animal pests.

It has already been disclosed that certain oxazoline derivatives have insecticidal and acaricidal properties (cf., for example, EP-A 0345775 and EP-A 0432661).

However, the activity of these prior-art compounds is not entirely satisfactory in all fields of application, in particular at low application rates and concentrations.

The new azatrioxaspiroalkenes of the formula (I)

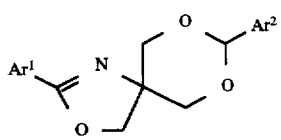     (I)

in which

Ar¹ and Ar² are identical or different and independently of one another in each case represent optionally substituted aryl, have now been found.

Furthermore, it has been found that azatrioxaspiroalkenes of the formula (I) are obtained by a process which comprises (a) reacting amino alcohols of the formula (II)

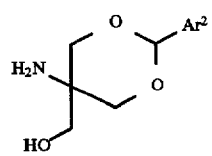     (II)

in which

Ar² has the abovementioned meaning, and carboxylic acids of the formula (III)

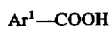     (III)

in which

Ar¹ has the abovementioned meaning, with a dehydrating agent, if appropriate in the presence of a diluent, or (b) reacting amide alcohols of the formula (IV)

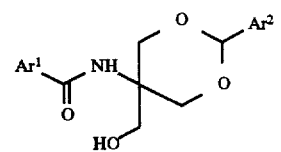     (IV)

in which

Ar¹ and Ar² have the abovementioned meanings, with a dehydrating agent, if appropriate in the presence of a diluent, or (c) reacting carboxamides of the formula (V)

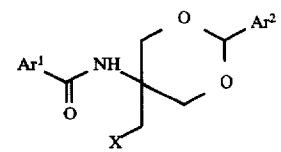     (V)

in which

Ar¹ and Ar² have the abovementioned meanings and x represents halogen, alkylsulfonyloxy or arylsulfonyloxy, with a base, if appropriate in the presence of a diluent, or (d) reacting carboxamide benzoates of the formula (VI)

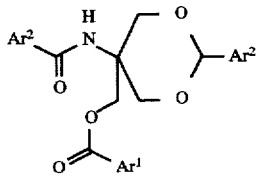

in which

Ar¹ and Ar² have the abovementioned meanings, with a base, if appropriate in the presence of a diluent.

Furthermore, it has been found that azatrioxaspiroalkenes of the formula (I) are highly suitable for combating animal pests. They are distinguished, in particular, by a high activity against arthropods and nematodes. The azatrioxaspiroalkenes of the formula (I) can be employed as a stereoisomer mixture as well as in the form of their pure E or Z isomers.

Surprisingly, the azatrioxaspiroalkenes of the formula (I) according to the invention show a considerably better activity against animal pests than the prior-art compounds of the most similar constitution.

Formula (I) provides a general definition of the compounds according to the invention.

Preferred substituents or ranges of the radicals listed in the formulae mentioned hereinabove and hereinbelow are illustrated in the following text.

Ar¹ preferably represents phenyl which is optionally mono-substituted to pentasubstituted by identical or different substituents from the series consisting of halogen, cyano, nitro, hydroxyl, $C_1-C_6$-alkyl, $C_1-C_6$-alkoxy, $C_1-C_6$-alkylthio, $C_1-C_6$-halogenoalkyl, $C_1-C_6$-halogenoalkoxy or $C_1-C_6$-halogenoalkylthio.

Ar² preferably represents phenyl which is optionally mono-substituted to pentasubstituted by identical or different substituents from the series consisting of halogen, cyano, nitro, hydroxyl, $C_1-C_{18}$-alkyl, $C_1-C_8$-halogenoalkyl, $C_1-C_8$-alkoxy-$C_1-C_8$-alkyl, $C_1-C_{18}$-alkoxy (in which individual methylene groups are optionally replaced by oxygen atoms), $C_1-C_8$-halogenoalkoxy, $C_1-C_{18}$-alkylthio, $C_1-C_8$-halogenoalkylthio, $C_1-C_8$-alkyl-carbonyl, $C_1-C_8$-halogenoalkyl-carbonyl, $C_1-C_8$-alkoxy-carbonyl, $C_1-C_8$-halogenoalkoxy-carbonyl, $C_1-C_3$-alkylenedioxy, $C_1-C_3$-halogenoalkylenedioxy, or cyclohexyl, cyclohexylmethyl or cyclohexyloxy, each of which is optionally substituted by $C_1-C_6$-alkyl, $C_1-C_6$-alkoxy, cyclohexyl or phenyl, or pyridyloxy which is optionally monosubstituted to trisubstituted by identical or different substituents from the series consisting of halogen, $C_1-C_4$-alkyl or $C_1-C_4$-halogenoalkyl, or phenyl, benzyl, benzoyl, phenoxy, phenylthio, benzyloxy or benzylthio, each of which is optionally monosubstituted to tetrasubstituted by identical or different substituents from the series consisting of halogen, $C_1-C_6$-alkyl, $C_1-C_6$-halogenoalkyl, $C_1-C_6$-alkoxy, $C_1-C_6$-halogenoalkoxy, $C_1-C_6$-alkoxy-$C_1-C_6$-alkyl, $C_1-C_6$-alkoxy-ethyleneoxy, $C_1-C_6$-alkylthio or $C_1-C_6$-halogenoalkylthio.

The hydrocarbon radicals, such as alkyl, which are mentioned above in the definition of the compounds according to the invention are, as far as this is possible, in each case straight-chain or branched, also in connection with hetero atoms, such as alkoxy.

Ar¹ particularly preferably represents phenyl which is is optionally monosubstituted to trisubstituted by identical or different substituents from the series consisting of fluorine, chlorine, bromine, cyano, nitro, hydroxyl, or methyl, ethyl, n- or i-propyl, methoxy, ethoxy, n- or i-propoxy, methylthio, ethylthio, n- or i-propylthio, each of which is optionally substituted by fluorine and/or chlorine.

Ar² particularly preferably represents phenyl which is optionally monosubstituted to tetrasubstituted by identical or different substituents from the series consisting of fluorine, chlorine, bromine, cyano, nitro, hydroxyl, or methyl, ethyl, n- or i-propyl, n-, i-, s- or t-butyl, n-, i-, s- or t-pentyl, n-, i-, s- or t-hexyl, n- or i-octyl, n- or i-nonyl, n- or i-decyl, n- or i-dodecyl, methoxy, ethoxy, n- or i-propoxy, n-, i-, s- or t-butoxy, n-, i-, s- or t-pentyloxy, n-, i-, s- or t-hexyloxy, n- or i-octyloxy, n- or i-nonyloxy, n- or i-decyloxy, n- or i-dodecyloxy, methylthio, ethylthio, n- or i-propylthio, n-, i-, s- or t-butylthio, n-, i-, s- or t-pentylthio, n-, i-, s- or t-hexylthio, n- or i-octylthio, n- or i-nonylthio, n- or i-decylthio, n- or i-dodecylthio, acetyl, propionyl, n- or i-butyroyl, n-, i-, s- or t-valeroyl, methoxycarbonyl, ethoxycarbonyl, n- or i-propoxycarbonyl, n-, i-, s- or t-butoxycarbonyl, n-, i-, s- or t-pentoxycarbonyl, methylenedioxy, ethylenedioxy, each of which is optionally substituted by fluorine and/or chlorine, or cyclohexyl, cyclohexylmethyl or cyclohexyloxy, each of which is optionally substituted by methyl, ethyl, n- or i-propyl, n-, i-, s- or t-butyl, methoxy, ethoxy, n- or i-propoxy, n-, i-, s- or t-butoxy, cyclohexyl or phenyl, or pyridyloxy which is optionally monosubstituted to trisubstituted by identical or different substituents from the series consisting of fluorine, chlorine, bromine, methyl, ethyl, n- or i-propyl, n-, i-, s- or t-butyl or trifluoromethyl, or phenyl, benzyl, benzoyl, phenoxy, phenylthio, benzyloxy or benzylthio, each of which is optionally monosubstituted to trisubstituted by identical or different substituents from the series consisting of fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, methylthio, ethylthio, n- or i-propylthio, n-, i-, s- or t-butylthio, difluoromethylthio or trifluoromethylthio.

Ar¹ very particularly preferably represents phenyl which is optionally monosubstituted or disubstituted by identical or different substituents from the series consisting of fluorine, chlorine, bromine, hydroxyl, methyl, ethyl, n- or i-propyl, methoxy, ethoxy, n- or i-propoxy, trifluoromethyl or trifluoromethoxy.

Ar² very particularly preferably represents phenyl which is optionally monosubstituted to trisubstituted by identical or different substituents from the series consisting of fluorine, chlorine, bromine, cyano, nitro, hydroxyl, or methyl, ethyl, n- or i-propyl, n-, i-, s- or t-butyl, n-, i-, s- or t-pentyl, n-, i-, s- or t-hexyl, n- or i-octyl, n- or i-nonyl, n- or i-decyl, n- or i-dodecyl, methoxy, ethoxy, n- or i-propoxy, n-, i-, s- or t-butoxy, n-, i-, s- or t-pentyloxy, n-, i-, s- or t-hexyloxy, n- or i-octyloxy, n- or i-nonyloxy, n- or i-decyloxy, n- or i-dodecyloxy, methylthio, ethylthio, n- or i-propylthio, n-, i-, s- or t-butylthio, n-, i-, s- or t-pentylthio, n-, i-, s- or t-hexylthio, n- or i-octylthio, n- or i-nonylthio, n- or i-decylthio, n- or i-dodecylthio, acetyl, propionyl, n- or i-butyroyl, n-, i-, s- or t-valeroyl, methoxycarbonyl, ethoxycarbonyl, n- or i-propoxycarbonyl, n-, i-, s- or t-butoxycarbonyl, n-, i-, s- or t-pentoxycarbonyl, methylenedioxy, ethylenedioxy, each of which is optionally substituted by fluorine and/or chlorine, or cyclohexyl, cyclohexylmethyl or cyclohexyloxy, each of which is optionally substituted by methyl, ethyl, n- or i-propyl, n-, i-, s- or t-butyl, methoxy, ethoxy, n- or i-propoxy, n-, i-, s- or t-butoxy, cyclohexyl or phenyl, or pyridyloxy which is optionally monosubstituted to trisubstituted by identical or different substituents from the series consisting of fluorine, chlorine, bromine, methyl, ethyl, n- or i-propyl, n-, i-, s- or t-butyl or trifluoromethyl, or phenyl, benzyl, benzoyl, phenoxy, phenylthio, benzyloxy or benzylthio, each of which is optionally monosubstituted to trisubstituted by identical or different substituents from the series consisting of fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, methylthio, ethylthio, n- or i-propylthio, n-, i-, s- or t-butylthio, difluoromethylthio or trifluoromethylthio.

The definitions of radicals which have been mentioned above in general or in preferred ranges apply both to the end products of the formula (I) and, analogously, to the starting substances or intermediates required in each case for the preparation, to the isomer mixtures and to the pure E or Z isomers.

These definitions of radicals can be combined as desired with each other, that is to say that combinations between the abovementioned ranges of preferred compounds are also possible.

Preferred compounds of the formula (I) according to the invention are those which combine the meanings mentioned above as being preferred (preferable).

Particularly preferred compounds of the formula (I) according to the invention are those which combine the meanings mentioned above as being particularly preferred.

Very particularly preferred compounds of the formula (I) according to the invention are those which combine the meanings mentioned above as being very particularly preferred.

The following meanings of group Ar¹ in formula (I) may be mentioned by way of example:

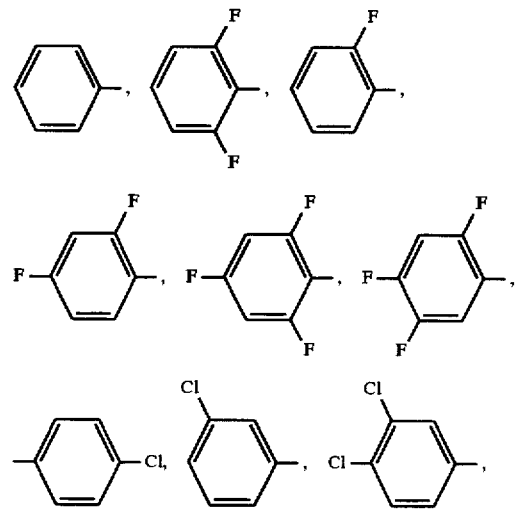

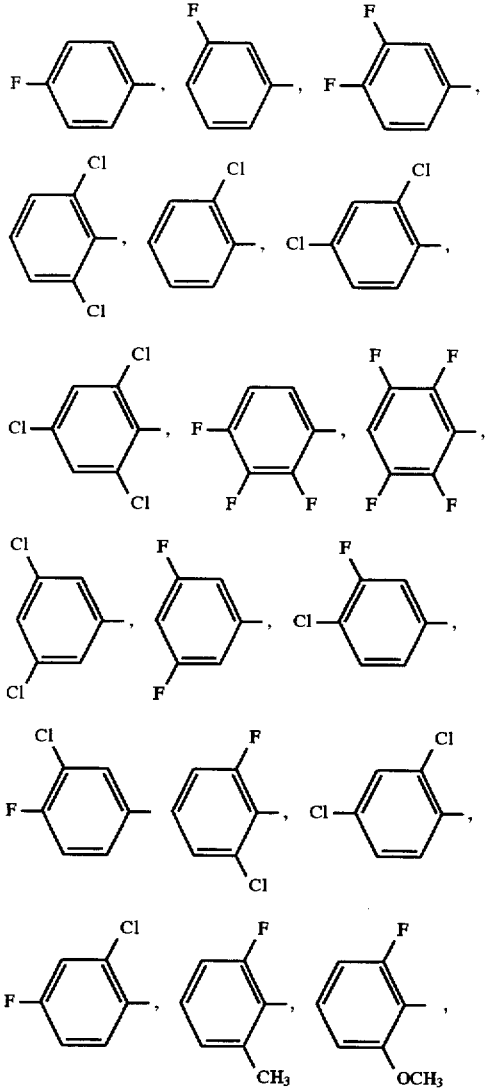

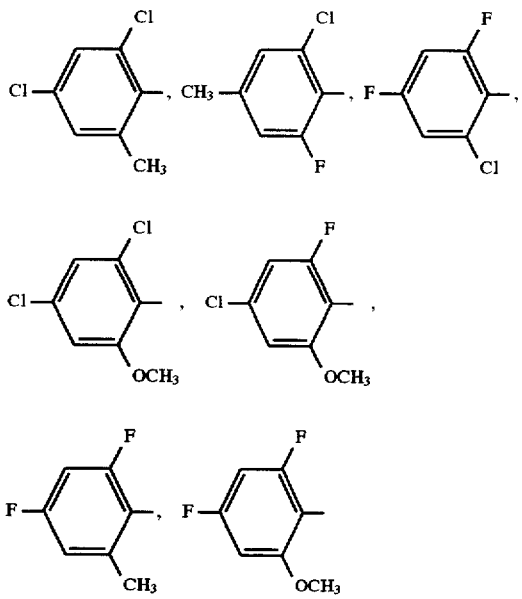

The following meanings of group Ar² in formula (I) may be mentioned by way of example:

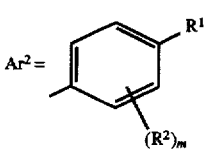

R¹=in accordance with Table 1
(R²)=in accordance with Table 2

| TABLE 1 | |
|---|---|
| R¹ | R¹ |
| H | $-OCF_2CHFCF_3$ |
| Br | $-OCF_2CHFCF_3$ |
| Cl | $-OCF_2CHFCF_3$ |
| F | $-CH_2CH_2-O-C_2H_5$ |
| $CH_3$ | $-CH_2CH_2-O-C_2H_5$ |
| $C_2H_5$ | $-CH_2CH_2-O-C_2H_5$ |
| $C_3H_{7\text{-}n}$ | $-CH_2CH_2-O-C_4H_9\text{-}n$ |
| $C_3H_{7\text{-}i}$ | $-CH_2CH_2-O-C_4H_9\text{-}n$ |
| $-C_4H_9\text{-}n$ | $-CH_2CH_2-O-C_4H_9\text{-}n$ |
| $-C_4H_9\text{-}i$ | $-CH_2CH_2-O-C_4H_9\text{-}n$ |
| $-C_4H_9\text{-}t$ | $-CH_2CH_2-O-C_4H_9\text{-}n$ |
| $-C_6H_{13}\text{-}n$ | $-CH_2CH_2-O-C_6H_{13}\text{-}n$ |
| $-C_{12}H_{25}\text{-}n$ | $-C_5H_{11}\text{-}t$ |
| $-C_{10}H_{21}\text{-}n$ | $-SC_4H_9\text{-}n$ |
| $-C_8H_{17}\text{-}n$ | $-SC_6H_{13}\text{-}n$ |
| $-C_9H_{19}\text{-}n$ | $-SC_8H_{17}\text{-}n$ |
| $CF_3$ | $-SC_{12}H_{25}\text{-}n$ |
| $-CF_2CHF_2$ | $-SCF_3$ |
| $-OC_6H_{13}\text{-}n$ | $-SCF_2CHF_2$ |
| $-OCH_3$ | $-SCF_2CHF_2$ |
| $-OC_2H_5$ | $-SCF_2CHF_2$ |
| $-OC_3H_7$ | $-SCF_2CHF_2$ |

TABLE 1-continued

| $R^1$ | $R^1$ |
|---|---|
| $-OC_3H_7$-i | $-SCF_2CHF_2$ |
| $-OC_4H_9$-n | $-SCF_2CHF_2$ |
| $-OC_4H_9$-i | $-SCF_2CHF_2$ |
| $-OC_4H_9$-t | $-SCF_2CHF_2$ |
| $-OC_8H_{17}$-n | $-SCF_2CHFCH_3$ |
| $-OC_{12}H_{25}$-n | $-CO-CH_3$ |
| $-OCF_3$ | ⬡–H |
| $-OCF_2CHF_2$ | –⬡(H)–$C_4H_9$-t |
| $-OCH_2CF_3$ | $-O-$⬡–H |
| $-OCF_2CHFCl$ | $-O-$⌬$-C_4H_9$-t |
| $-CO-C_4H_9$-i | –⌬ |
| –⌬–Cl | –⌬–$C_4H_9$-i |
| –⌬–Br | –⌬–$C_4H_9$-s |
| –⌬–$C_4H_9$-s | –⌬(Cl)–$CH_3$ |
| –⌬(Cl,Cl) | –⌬(Cl)–$C_3H_7$-n |
| –⌬($CH_3O$)–Cl | –⌬–$OC_2H_5$ |
| $-\underset{O}{\overset{\parallel}{C}}$–⌬–Cl | –⌬–$CF_3$ |

TABLE 1-continued

| R¹ | R¹ |
|---|---|
| −C(=O)−C₆H₄−OCF₃ (para) | 2-Cl, 4-CF₃ phenyl |
| −C₆H₄−C₃H₇-n (para) | 2-CH₃, 4-CF₃ phenyl |
| −C(=O)−C₆H₄−CF₃ (para) | 2-CH₃O, 4-CF₃ phenyl |
| −C₆H₄−C₄H₉-n (para) | −C₆H₄−OCF₃ (para) |
| −C₆H₄−OCHF₂ (para) | −CH₂−C₆H₄−CF₃ (para) |
| 2,6-Cl₂, 4-CF₃ phenyl | −CH₂−C₆H₄−OCF₃ (para) |
| 2,6-(CH₃)₂, 4-CF₃ phenyl | −O−C₆H₅ |
| −CH₂−C₆H₅ | −O−C₆H₄−Cl (para) |
| −CH₂−C₆H₄−F (para) | −O−C₆H₄−Br (para) |
| −CH₂−C₆H₄−Cl (para) | −O−C₆H₄−CH₃ (para) |
| −CH₂−C₆H₄−Br (para) | −O−C₆H₄−C₃H₇-n (para) |
| −CH₂−C₆H₄−C₄H₉-t (para) | −O−C₆H₄−C₃H₇-i (para) |

TABLE 1-continued

| R¹ | R¹ |
|---|---|
| —CH₂—C₆H₄—C₆H₁₃-n | —O—C₆H₄—OC₂H₅ |
| —CH₂—C₆H₄—C₁₂H₂₅-n | —O—C₆H₃(CH₃)—OCH₃ |
| —CH₂—C₆H₄—OC₂H₅ | —O—C₆H₃(Cl)—OC₂H₅ |
| —O—C₆H₃(Cl)—OCH₃ | —O—C₆H₄—OCF₃ |
| —O—C₆H₃(CH₃)—Cl | —O—C₆H₄—OCHF₂ |
| —O—C₆H₂(Cl)₂—OCH₃ | —O—C₆H₄—OCH₂CF₃ |
| —O—C₆H₄—CH₂CH₂OC₂H₅ | —O—C₆H₄—OCF₂CHF₂ |
| —O—C₆H₄—CF₃ | —O—C₆H₄—OCF₂CHClF |
| —O—C₆H₃(CH₃)—CF₃ | —O—C₆H₄—OCF₂CHFCF₃ |
| —O—C₆H₃(OCH₃)—CF₃ | —CO—C₆H₅ |
| —O—C₆H₃(Cl)—CF₃ | —O—C₆H₂(Cl)₂—CF₃ |

TABLE 1-continued
| $R^1$ | $R^1$ |
|---|---|
| 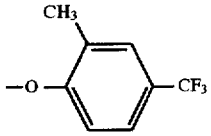 | 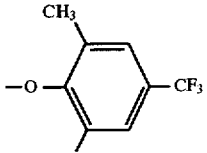 |
| 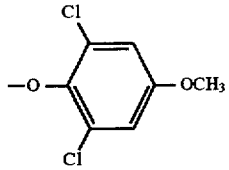 | 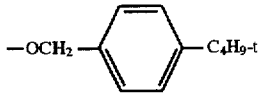 |
| 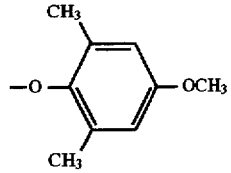 | 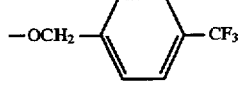 |
| 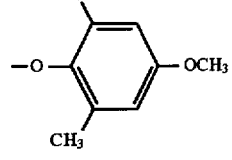 | 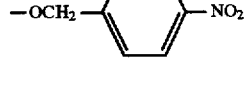 |
| 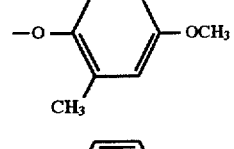 | 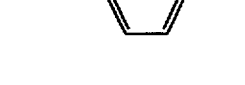 |
| 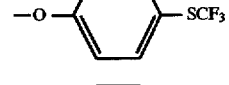 | 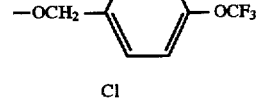 |
| 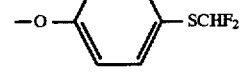 | 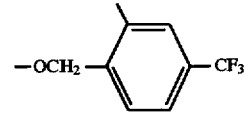 |
| 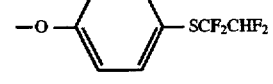 | 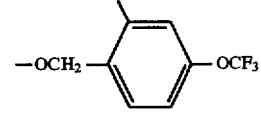 |
| 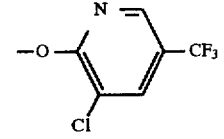 | 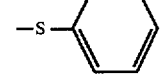 |
|  | 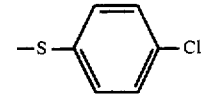 |

TABLE 1-continued

| R¹ | R¹ |
|---|---|
| -O-(3-Cl,4-SCH₃-phenyl) | -S-(4-Br-phenyl) |
| -OCH₂-(4-Cl-phenyl) | -S-(4-CF₃-phenyl) |
| -OCH₂-(4-Br-phenyl) | -S-(4-OCF₃-phenyl) |
| -OCH₂-(2-Cl,4-Cl-phenyl) | -S-(4-OCF₃-phenyl) |
| -CO-O-C₄H₉-t<br>-CN | -CO-O-C₃H₇-i |

TABLE 2

| (R²)ₘ | (R²)ₘ |
|---|---|
| H | 2-CH₃ |
|  | 3,5-(CH₃)₂ |
|  | 2,6-(CH₃)₂ |
| 2-Cl | 2-OCH₃ |
| 2-F | 3-OCH₃ |
| 3-Cl | 2,6-OC₂H₅ |
| 2,6-Cl₂ | 3-CH₃ |
| 3,5-Cl₂ | 3,5-OCH₃ |
| 3,5-F₂ | 3-OC₆H₅ |
| 2,5-Cl₂ | 2-Cl; 5-CF₃ |
| 3,5-Cl₂; 2-F | 2-Cl; 3-CF₃ |
| 2,3-F₂ |  |
| 2,5-F₂ | together with R¹ represents |
| 2,3,5,6-Cl₄ | 3,4-OCF₂O— |
| 3-CF₃ | 3,4-OCF₂CF₂O |

Table 3 below gives examples of the compounds of the formula (Ia) according to the invention:

$$\text{Ar}^1-\text{C}(=\text{N})-\text{[dioxane-CH}_2\text{O]}-\text{C}_6\text{H}_{4-m}(\text{R}^2)_m-\text{R}^1 \quad (\text{Ia})$$

TABLE 3

Examples of the compounds of the formula (Ia)

| Ar¹ | R¹ | (R²)ₘ |
|---|---|---|
| 2,6-difluorophenyl | Cl | 2-Cl, 3-CF₃ |
| 2,6-difluorophenyl | -O-(2-Cl,4-CF₃-phenyl) | — |
| 2,6-difluorophenyl | -CF₃ | — |
| 2,6-difluorophenyl | -C(CH₃)₃ | — |

TABLE 3-continued

Examples of the compounds of the formula (Ia)

| Ar¹ | R¹ | (R²)ₘ |
|---|---|---|
| 2,6-difluorophenyl | $-S-C_4H_9\text{-}t$ | — |
| 2,6-difluorophenyl | Cl | 2-Cl, 5-CF₃ |
| 2,6-difluorophenyl | $-OCF_3$ | — |
| 2,6-difluorophenyl | $-OCF_2CHF_2$ | — |
| 2,6-difluorophenyl | $-OCF_2-CHF-CF_3$ | 2,5-Cl₂ |
| 2,6-difluorophenyl | $-OCF_2-CHF-Cl$ | 2,5-Cl₂ |
| 2,6-difluorophenyl | $-O-\text{C}_6\text{H}_4\text{-Cl}$ (4-Cl-phenoxy) | 3,5-Cl₂ |
| 2,6-difluorophenyl | 2-Cl-4-CF₃-phenoxy ($-O-$) | 2-F |
| 2,6-difluorophenyl | 3-Cl-5-CF₃-pyridin-2-yloxy ($-O-$) | 3,5-Cl₂ |
| 2,6-difluorophenyl | $-CF_2-CHF_2$ | 3,5-Cl₂ |
| 2,6-difluorophenyl | F | 2-F; 3,5-Cl₂ |
| 2,6-difluorophenyl | F | 2-F; 3,5-Cl₂ |
| 2,6-difluorophenyl | 4-OCHF₂-phenyl | — |
| 2,6-difluorophenyl | CF₃ | 2,3-F₂ |
| 2,6-difluorophenyl | CF₃ | 2,3,5-Cl₃ |
| 2,6-difluorophenyl | 2,6-Cl₂-4-CF₃-phenoxy ($-O-$) | 2-Cl |

TABLE 3-continued

Examples of the compounds of the formula (Ia)

| Ar¹ | R¹ | (R²)ₘ |
|---|---|---|
| 2,6-diF-C₆H₃ | —C₆H₅ | — |
| 2,6-diF-C₆H₃ | H | — |
| 2,6-diF-C₆H₃ | F | — |
| 2,6-diF-C₆H₃ | Cl | — |
| 2,6-diF-C₆H₃ | Br | — |
| 2,6-diF-C₆H₃ | —CH(CH₃)₂ | — |
| 2,6-diF-C₆H₃ | —C₆H₁₃-n | — |
| 2,6-diF-C₆H₃ | —C₁₀H₂₁-n | — |
| 2,6-diF-C₆H₃ | —SCF₃ | — |
| 2,6-diF-C₆H₃ | —C₆H₁₁ | — |
| 2,6-diF-C₆H₃ | —O—C₆H₁₁ | — |
| 2,6-diF-C₆H₃ | O—C₆H₅ | — |
| 2,6-diF-C₆H₃ | -(4-C₄H₉-t)-O—C₆H₄ | — |
| 2,6-diF-C₆H₃ | H | 2,3-Cl₂ |
| 2,6-diF-C₆H₃ | Cl | 2-Cl |
| 2,6-diF-C₆H₃ | H | 2,5-Cl₂ |

TABLE 3-continued

Examples of the compounds of the formula (Ia)

| Ar¹ | R¹ | (R²)ₘ |
|---|---|---|
| 2,6-difluoro-phenyl | —OCF₃ | 3,5-Cl₂ |
| 2,6-difluoro-phenyl | —CF₃ | 2,5-Cl₂, 3-F |
| 2,6-difluoro-phenyl | Cl | 2-Cl, 3,5-F₂ |
| 2,6-difluoro-phenyl | -2-Cl-4-CF₃—C₆H₃ | 3,5-Cl₂ |

Table 4

The compounds of Table 4 correspond to the compounds of the formula (Ia) listed in Table 3, but Ar¹ represents 2-chloro-6-fluoro-phenyl, and m, R¹ and R² have the meanings given in Table 3.

Table 5

The compounds of Table 5 correspond to the compounds of the formula (Ia) listed in Table 3, but Ar¹ represents 2,6-dichloro-phenyl, and m, R¹ and R² have the meanings given in Table 3.

Table 6

The compounds of Table 6 correspond to the compounds of the formula (Ia) listed in Table 3, but Ar¹ represents 2-chloro-phenyl, and m, R¹ and R² have the meanings given in Table 3.

Table 7

The compounds of Table 7 correspond to the compounds of the formula (Ia) listed in Table 3, but Ar¹ represents 2-fluoro-phenyl, and m, R¹ and R² have the meanings given in Table 3.

If, for example, 5-amino-5-hydroxymethyl-2-(4-methyl-phenyl)-1,3-dioxane and 2-chloro-benzoic acid are used as starting substances and polyphosphoric acid (PPA) is used as dehydrating agent for carrying out process (a) according to the invention, the course of the reaction can be outlined by the following equation:

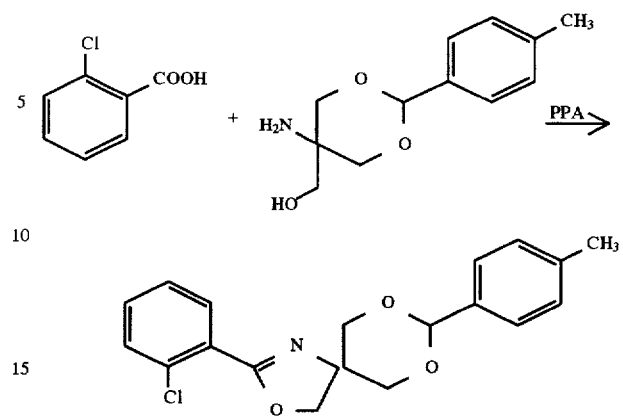

If, for example, 5-hydroxymethyl-5-(2-fluoro-benzoylamino)-2-(4-methoxy-phenyl)-1,3-dioxane is used as starting compound and polyphosphoric acid (PPA) as dehydrating agent for carrying out process (b) according to the invention, the course of the reaction can be outlined by the following equation:

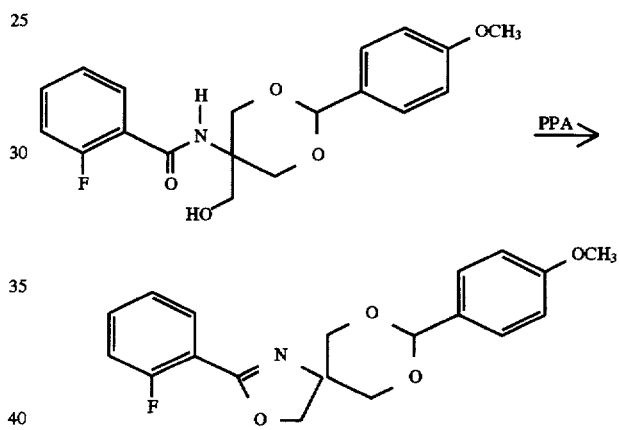

If, for example, 5-chloromethyl-S-(2-fluoro-benzoylamino)-2-(4-trifluoromethyl)-1,3-dioxane is used as is starting compound and triethylamine as the base for carrying out process (c) according to the invention, the course of the reaction can be outlined by the following equation:

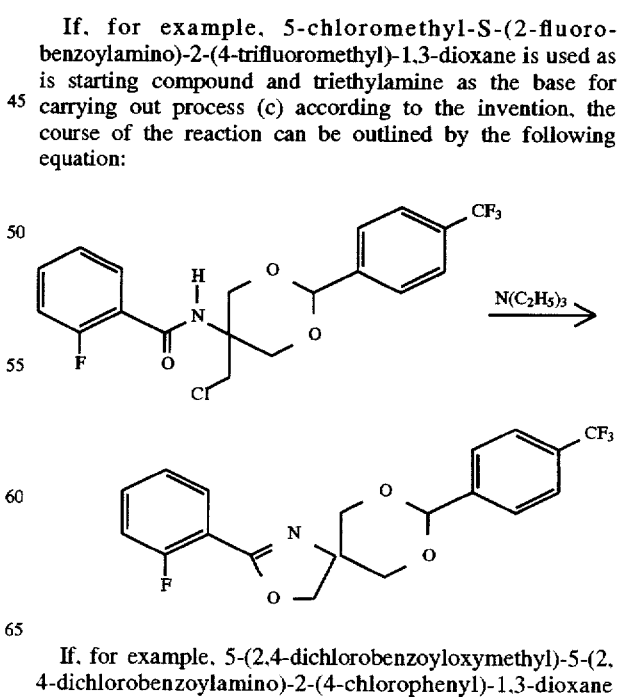

If, for example, 5-(2,4-dichlorobenzoyloxymethyl)-5-(2,4-dichlorobenzoylamino)-2-(4-chlorophenyl)-1,3-dioxane is used as starting compound and potassium tert-butylate as the base for carrying out process (d) according to the invention, the course of the reaction can be represented by the following equation:

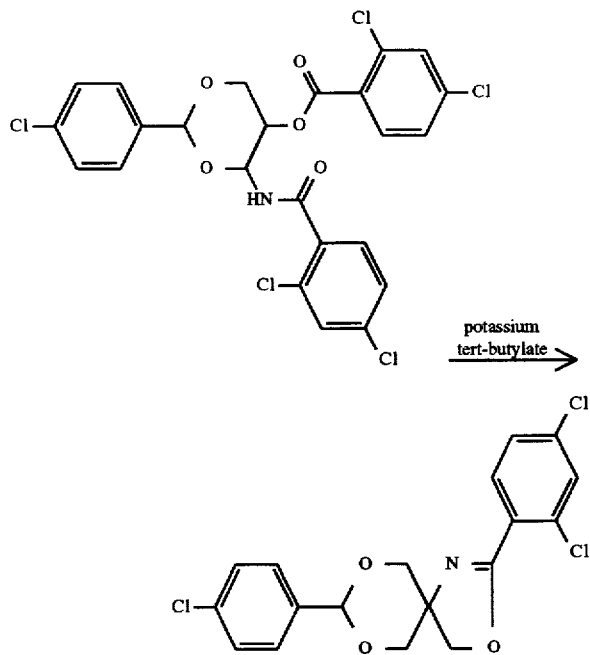

Formula (II) provides a general definition of the amino alcohols to be used as starting substances in the process according to the invention for the preparation of the compounds of the general formula (I). In formula (II), Ar² preferably, or in particular, has the meaning which has already been mentioned above in connection with the description of the compounds of the formula (I) as being preferred, or particularly preferred, for Ar².

With the exception of the compound of the formula (II) in which Ar² represents phenyl, the amino alcohols of the formula (II) were hitherto unknown from the literature; as new substances, they are part of the present application.

The new amino alcohols of the formula (II) are obtained when nitro alcohols of the formula (VII)

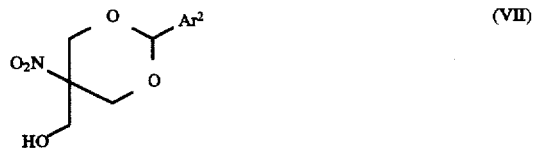

(VII)

in which

Ar² has the abovementioned meaning, are reacted with hydrogen in the presence of a catalyst such as, for example, Raney cobalt or Raney nickel, palladium or platinum (for example on carbon as support) at temperatures between −20° C. and +200° C., preferably between 0° C. and 150° C., and at pressures between 1 bar and 300 bar, preferably between 10 bar and 200 bar, if appropriate in the presence of a diluent such as, for example, methanol or ethanol (cf. the Preparation Examples).

Some of the nitro alcohols of the formula (VII) which are required as precursors are known and/or can be prepared by processes known per se (cf. J. Am. Chem. Soc. 63 (1941), 2635–2636; Synthesis 1993, 815–818, Preparation Examples).

With the exception of those compounds in which Ar² represents phenyl, 4-methoxy-phenyl, 4-cyano-phenyl, 2-nitro-phenyl, 3-nitro-phenyl, 4-nitro-phenyl, 4-chlorophenyl, 4-dimethylamino-phenyl, 4-hydroxyphenyl, 2-hydroxy-phenyl, 3-ethoxy-4-hydroxy-phenyl or 4-hydroxy-3-methoxy-phenyl, the nitro alcohols of the formula (VII) were hitherto not known from the literature and, as new substances, are part of the present application with the exception of the abovementioned compounds.

The nitro alcohols of the formula (VII) are obtained when aldehydes of the formula (VIII)

Ar²—CHO       (VIII)

in which

Ar² has the abovementioned meaning, are reacted with tris-hydroxymethyl-nitromethane, of the formula (IX)

(HOCH₂)₃C—NO₂       (IX), on a water separator at temperatures between 50° C. and 150° C. (cf. The Preparation Examples) in the presence of a solvent suitable for the azeotropic separation of water such as, for example, toluene, and in the presence of a catalyst such as, for example, p-toluenesulfonic acid, or when compounds of the formula (VII) are reacted with tris-hydroxymethyl-nitromethane, of the formula (IX), at −20° C. to 120° C. in the presence of acids or Lewis acids and a dehydrating reagent, for example trimethyl orthoformate.

Formula (III) provides a general definition of the carboxylic acids furthermore to be used as starting substances in process (a) according to the invention for the preparation of the compounds of the formula (I). In formula (III), Ar¹ preferably, or in particular, has the meaning which has already been mentioned above in connection with the description of the compounds of the formula (I) as being preferred, or particularly preferred, for Ar¹.

The starting substances of the formula (III) are known chemicals for organic synthesis.

Processes (a) and (b) according to the invention are carried out using a dehydrating agent. Dehydrating agents which can be employed are those customary in organic chemistry. The following are preferably suitable: sulfuric acid, polyphosphoric acid (PPA), phosphorus(V) oxide, dicyclohexylcarbodiimide (DCC), phosphorus(V) sulfide, sodium sulfate, calcium chloride, magnesium sulfate, trimethyl or triethyl orthoformate, molecular sieves, and the system triphenylphosphine/triethylamine/tetrachloromethane.

Suitable diluents for carrying out processes (a) to (c) according to the invention are the customary organic solvents. The following can preferably be used: aliphatic, alicyclic or aromatic, optionally halogenated hydrocarbons such as, for example, benzine, benzene, toluene, xylene, chlorobenzene, dichlorobenzene, petroleum ether, hexane, cyclohexane, tetraline, dichloromethane, chloroform, tetrachloromethane; ethers, such as t-butyl methyl ether, diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide and N,N-dimethylacetamide, N-methyl-pyrrolidone or hexamethylphosphoric triamide; esters, such as methyl acetate or ethyl acetate, and also sulfoxides, such as dimethyl sulfoxide, if appropriate also alcohols such as methanol, ethanol or n- or i-propanol, and furthermore organic basic solvents such as, for example, pyridine, picolines, lutidines or collidine.

When carrying out process (a) according to the invention, the reaction temperatures can be varied within a substantial range. In general, the process is carried out at temperatures between -20° C. and +200° C., preferably at temperatures between 0° C. and 150° C.

Process (a) according to the invention is generally carried out under atmospheric pressure. However, it is also possible to carry out the process under elevated or reduced pressure, in general between 0.1 bar and 10 bar.

To carry out process (a) according to the invention, the starting substances required in each case are generally employed in approximately equimolar amounts. However, it is also possible to use a larger excess of one of the two components employed in each case. In general, the reactions are carried out in a suitable diluent in the presence of a dehydrating agent, and the reaction mixture is stirred for several hours at the temperature required in each case. Working-up in the processes according to the invention is carried out in each case by customary methods.

In a particular embodiment of process (a) according to the invention, carboxylic acids of the formula (III) may also be replaced by corresponding nitrites, in which case a catalyst, such as, for example, zinc(II) chloride, is preferably used in place of a dehydrating agent.

Formula (IV) provides a general definition of the amide alcohols to be used as starting substances in process (b) according to the invention for the preparation of the compounds of the general formula (I). In formula (IV), $Ar^1$ and $Ar^2$ preferably, or in particular, have the meanings which have already been indicated above in connection with the description of the compounds of the formula (I) as being preferred, or particularly preferred, for $Ar^1$ and $Ar^2$.

The amide alcohols of the formula (IV) were hitherto not known from the literature; as new substances, they are part of the present application.

The new amide alcohols of the formula (IV) are obtained when amino alcohols of the formula (II)—above—are reacted with approximately equimolar amounts of carboxylic acid halides of the formula (X)

$$Ar^1—CO—X^1 \quad (X)$$

in which $Ar^1$ has the abovementioned meaning and $X^1$ represents halogen (preferably fluorine, chlorine or bromine, in particular chlorine), at temperatures between -80° C. and +200° C., preferably between -30° C. and +120° C., if appropriate in the presence of an acid acceptor such as, for example, pyridine, triethylamine or potassium carbonate, and if appropriate in the presence of a diluent such as, for example, toluene, tetrahydrofuran, acetone, methyl isobutyl ketone or acetonitrile.

When carrying out process (b) according to the invention, the reaction temperatures can be varied within a substantial range. In general, the process is carried out at temperatures between -20° C. and +150° C., preferably at temperatures between 0° C. and 100° C.

Process (b) according to the invention is generally carried out under atmospheric pressure. However, it is also possible to carry out the process under elevated or reduced pressure, in general between 0.1 bar and 10 bar.

For carrying out process (b) according to the invention for the preparation of the compounds of the formula (I), 1 to 20 mol, preferably 1 to 5 mol, of dehydrating agent are generally employed per mole of amide alcohol of the formula (IV).

In a preferred embodiment of process (b) according to the invention, the amide alcohol of the formula (IV) is introduced into a diluent, and the dehydrating agent is then metered in. The reaction mixture is stirred at the temperature required until the reaction has ended and subsequently worked up in the customary manner.

Formula (V) provides a general definition of the carboxamides to be used as starting substances in process (c) according to the invention for the preparation of the compounds of the general formula (I). In formula (V), $Ar^1$ and $Ar^2$ preferably, or in particular, have the meanings which have already been indicated above in connection with the description of the compounds of the formula (I) as being preferred, or particularly preferred, for $Ar^1$ and $Ar^2$; X preferably represents chlorine, bromine, methylsulfonyloxy, phenylsulfonyloxy or tolylsulfonyloxy, in particular chlorine and methylsulfonyl.

The carboxamides of the formula (V) were hitherto not known from the literature; as new substances, they are part of the present application.

The carboxamides of the formula (V) are obtained when corresponding amide alcohols of the formula (IV) are reacted with chlorinating agents such as, for example, phosgene, thionyl chloride, phosphorus(III) bromide or phosphorus (V) chloride, or with sulfonylating agents such as, for example, methanesulfonyl chloride, benzenesulfonyl chloride or p-toluenesulfonyl chloride, at temperatures between -20° C. and 150° C., if appropriate in the presence of a diluent such as, for example, methylene chloride, tetrahydrofuran, toluene, chlorobenzene, pyridine or tetrachloromethane.

Process (c) according to the invention is carried out in the presence of a base. Suitable bases are all customary inorganic or organic bases. The following can preferably be used: the hydrides, oxides, hydroxides, amides, alcoholates, acetates, carbonates or hydrogen carbonates of alkaline earth metals or alkali metals such as, for example, sodium hydride, calcium hydride, calcium oxide, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines such as trimethylamine, triethylamine, tributylamine, N,N-dimethylaniline, pyridine, picoline, lutidine, collidine, N-methylpiperidine, N,N-dimethylamino-pyridine, diazabicyclooctane (DABCO), diazabicyclononene (DBN) or diazabicycloundece is also possible to use the tertiary amines as solvents.

When carrying out process (c) according to the invention, the reaction temperatures can be varied within a substantial range. In general, the process is carried out at temperatures between -20° C. and +200° C., preferably at temperatures between 10° C. and 150° C.

Process (c) according to the invention is generally carried out under atmospheric pressure. However, it is also possible to carry out the process under elevated or reduced pressure, in general between 0.1 bar and 10 bar.

For carrying out process (c) according to the invention for the preparation of the compounds of the formula (I), 1 to 3 mol, preferably 1.0 to 1.5 mol, of a base are generally employed per mole of carboxamide of the formula (V).

In a preferred embodiment of process (c) according to the invention, the carboxamide of the formula (V) is first prepared from an amide alcohol of the formula (IV) as indicated above (cf. also the Preparation Examples), the mixture is concentrated under reduced pressure, and the crude product of formula (V) obtained as the residue is mixed with a base in a suitable diluent; the mixture is stirred at the temperature required until the reaction is complete and subsequently worked up in the customary manner (cf. the Preparation Examples).

In a further preferred embodiment of process (c) according to the invention, the carboxamide of the formula (V) is first prepared in a basic solvent, in particular pyridine, as indicated above, and the compounds of the formula (I) are subsequently generated at elevated temperature.

The carboxamide benzoates of the formula (VI), which are used in process (d) according to the invention for the preparation of the compounds of the general formula (I), were hitherto not known from the literature and, as new substances, are part of the present application. In formula (VI), $Ar^1$ and $Ar^2$ preferably, or in particular, have the meanings which have already been indicated above in connection with the description of the compounds of the formula (I) as being preferred, or particularly preferred, for $Ar^1$ and $Ar^2$.

For example, the carboxamide derivatives of the formula (VI) are obtained when amino alcohols of the formula (II) are reacted with approximately twice the equimolar amount of carboxylic acid halide of the formula (X) at temperatures between −80° C. and 200° C., preferably between −30° C. and 120° C., if appropriate in the presence of an acid acceptor such as, for example, pyridine, triethylamine or potassium carbonate, and if appropriate in the presence of a diluent such as, for example, toluene, tetrahydrofuran, acetone, methyl isobutyl ketone or acetonitrile.

The active compounds are suitable for combating animal pests, preferably arthropods and nematodes, in particular insects and arachnids, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia Bpp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis,* Ceratophyllus spp., Ctenocephalides spp. and Pulex spp.

From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., Trichodorus spp.

The compounds of the formula (I) according to the invention also show a fungicidal activity.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound as well as very fine capsules in polymeric substances and in coating compositions for seed, and in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ammonium salts, and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The following compounds may be mentioned:
acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mevinphos, mesulfenphos, methacrifos, methamidophos, naled, omethoate, oxydemeton M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridinyl)methyl]-N'-cyano-N-methyl-ethaneimideamide (NI-25), abamectin, amitrazin, avermectin, azadirachtin, bensultap, *Bacillus thuringiensis*, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimiphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds according to the invention are not only active against plant, hygiene and stored-product pests, but also, in the veterinary medicine sector, against animal parasites (ectoparasites and endoparasites) such as scaly ticks, Argasidae, scab mites, Trombidae, flies (stinging and sucking), parasitic fly larvae, lice, hair lice, bird lice, fleas and endoparasitic worms. For example, they show an outstanding activity against ticks such as, for example, *Boophilus microplus*.

The active compounds of the formula (I) according to the invention are also suitable for combating arthropods which attack agricultural livestock such as, for example, cattle, sheep, goats, horses, pigs, donkeys, camels, buffalo, rabbits, chickens, turkeys, ducks, geese, honey bees, other domestic animals such as, for example, dogs, cats, cage birds and aquarium fish, and so-called laboratory animals such as, for example, hamsters, guinea pigs, rats and mice. By combating these arthropods, it is intended to reduce deaths and decreasing performance (in the case of meat, milk, wool, hides, eggs, honey and the like), so that more economical and simpler animal husbandry is possible by using the active compounds according to the invention.

The application of the active compounds according to the invention in the veterinary sector occurs in a known fashion by enteral application in the form of, for example, tablets, capsules, potions, drenches, granules, pastes, boli, the feed-through process, suppositories, by parenteral application such as, for example, by means of injections (intramuscular, subcutaneous, intravenous, intraperitoneal and the like), implants, by nasal application, by dermal application, for example in the form of bathing or dipping, spraying, pouring on, spotting on, washing, dusting, and with the aid of molded articles containing active compound, such as collars, ear tags, tail tags, limb bands, halters, marking devices and the like.

Preparation and use of the substances according to the invention are illustrated by the examples which follow.

PREPARATION EXAMPLES

Example I-1

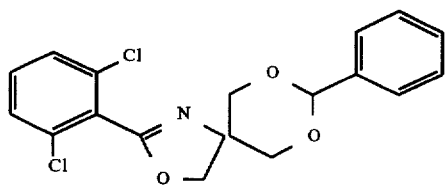

3.4 g (8.7 mmol) of 2-phenyl-5-(2,6-dichlorobenzoylamino)-5-hydroxymethyl-1,3-dioxane are suspended in 50 ml of toluene, and the suspension is stirred with 2 g of thionyl chloride for 24 hours at 80° C. Excess thionyl chloride and toluene are then distilled off under a water pump vacuum.

The residue is taken up in 50 ml of toluene and 0.9 g of potassium t-butylate is added. The reaction mixture is then stirred at 50C and checked by thin-layer chromatography. When the reaction is complete, the solution obtained is washed with water, and the organic phase is subsequently concentrated under a water pump vacuum. The residue is chromatographed on silica gel using cyclohexane/ethyl acetate (2:1 by volume).

1 g (31% of theory) of 8-phenyl-2-(2,6-dichloro-phenyl)-1-aza-3,7,9-trioxaspiro|4.5|dec-1-ene of melting point 158° C.–160° C. is obtained.

The compounds of the formula (I) listed in Table 8 were prepared in accordance with processes a–d:

TABLE 8

| Ex. No. | Ar¹ | R¹ | R²$_m$ | Isomer | M.p. °C. |
|---|---|---|---|---|---|
| I-2 | 2,6-diCl-phenyl | t-C$_4$H$_9$ | — | cis | 207–209 |
| I-3 | 2,4-diCl-phenyl | H | — | cis | 130–132 |
| I-4 | 2-Cl-phenyl | H | — | cis | oil |
| I-5 | 2,6-diF-phenyl | t-C$_4$H$_9$ | — | cis | oil |
| I-6 | 4-Cl-phenyl | H | — | cis | oil |

TABLE 8-continued (I) [structure with R¹, R²m on phenyl connected via dioxane ring to N-Ar¹]

| Ex. No. | Ar¹ | R¹ | R²m | Isomer | M.p. °C. |
|---|---|---|---|---|---|
| I-7 | 2,4-dichlorophenyl | Cl | — | cis | 124–125 |
| I-8 | 4-chlorophenyl | Cl | 3-Cl | cis | 192 |
| I-9 | 4-chlorophenyl | Cl | — | cis | 210 |
| I-10 | 2,6-difluorophenyl | Cl | — | cis | 154–155 |
| I-11 | 3,4-dichlorophenyl | Cl | 2-Cl | cis | 168–170 |
| I-12 | 2,6-dichlorophenyl | Cl | 2-Cl | cis | 184–186 |
| I-13 | 2-chloro-4-hydroxyphenyl | Cl | — | cis | 222–224 |
| I-14 | 2,6-difluorophenyl | Cl | 2-Cl | cis | 158–160 |
| I-15 | 2-fluoro-6-hydroxyphenyl | Cl | 2-Cl | cis | oil |
| I-16 | 4-chlorophenyl | Cl | 2-Cl | cis | 212 |

Starting substances of the formula (II)

EXAMPLE (II-1)

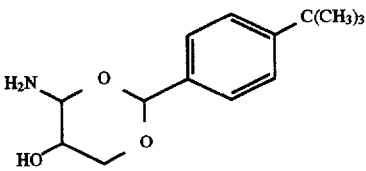

10 ml of triethylamine and 10 g of palladium/charcoal are added to 104 g (0.35 mol) of 2-(4-t-butyl-phenyl)-5-hydroxymethyl-5-nitro-1,3-dioxane in 1 liter of ethanol, and the mixture is hydrogenated for 3 days at 20° C. and 30 bar. It is then filtered, the filtrate is concentrated under a water pump vacuum, the residue is digested using n-hexane, and the product obtained as crystals is isolated by filtration with suction.

43 g (47% of theory) of (cis)-2-(4-t-butyl-phenyl)-5-hydroxymethyl-5-amino-1,3-dioxane of melting point 138° C.–140° C. are obtained.

The compounds of the formula (II) listed in Table 9 were obtained analogously to Example (II-1):

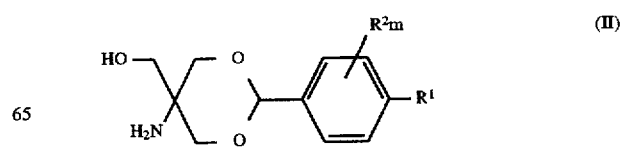

TABLE 9

| Ex. No. | R¹ | R²ₘ | Isomer | M.p. °C. |
|---|---|---|---|---|
| II-2 | Cl | — | trans | 149–150 |
| II-3 | Cl | — | cis | 168–170 |
| II-4 | t-C₄H₉ | — | trans | 176–178 |
| II-5 | Cl | 2-Cl | cis | 155 |

Starting substances of the formula (IV).

EXAMPLE (IV-1)

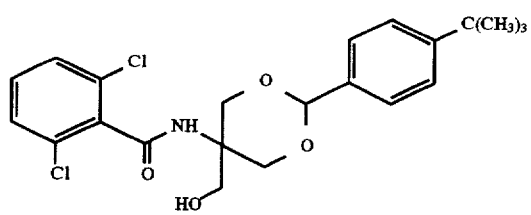

5 ml of triethylamine are added to 5 g (20 nmol) of 2-(4-t-butyl-phenyl)-5-amino-5-hydroxymethyl-1,3-dioxane in 80 ml of methylene chloride. A solution of 4.5 g (20 mmol) of 2,6-dichloro-benzoyl chloride in 5 ml of methylene chloride is then added dropwise at 0° C., and the mixture is stirred for 15 hours at 20° C. The mixture is subsequently washed using 0.5N sodium hydroxide solution, and the organic phase is dried using sodium sulfate and filtered. The filtrate is concentrated under a water pump vacuum, the residue is crystallized by digestion with n-hexane, and the product is isolated by filtration with suction.

7.2 g (83% of theory) of 2-(4-t-butyl-phenyl)-5-hydroxymethyl-5-(2,6-dichloro-benzoyl-amino)-1,3-dioxane of melting point 178° C.–180° C. are obtained.

The compounds of the formula (IV) listed in Table 10 below were also prepared analogously to Example (IV-1).

TABLE 10

Ar¹—CO—NH, HO— structure with O, O, R¹, R²ₘ (IV)

| Ex. No. | Ar¹ | R¹ | R²ₘ | Isomer | Melting point (°C.) |
|---|---|---|---|---|---|
| IV-2 | 2,3-di-Cl-phenyl | H | — | cis | 164 |
| IV-3 | 3-F-phenyl | H | — | cis | 164 |
| IV-4 | 2,6-di-F-phenyl | H | — | cis | 159–160 |
| IV-5 | 2,3-di-Cl-phenyl | Cl | — | cis | 172–174 |
| IV-6 | 2,4-di-Cl-phenyl | H | — | cis | 174 |
| IV-7 | 2,6-di-F-phenyl | 4-t-C₄H₉ | — | | |
| IV-8 | 2-Cl-phenyl | H | — | cis | 174 |
| IV-9 | 4-Cl-phenyl | H | — | trans | 120–122 |
| IV-10 | 2-F-phenyl | H | — | cis | 98–100 |
| IV-11 | 2-Cl-phenyl | H | — | | |
| IV-12 | 2-Cl-phenyl | 4-t-C₄H₉ | — | cis | 174–176 |

TABLE 10-continued

![structure IV]

Ar¹—CO—NH—C(CH₂OH)(CH₂-O-)... (IV) with dioxane ring bearing Ar with R¹ and R²ₘ

| Ex. No. | Ar¹ | R¹ | R²ₘ | Isomer | Melting point (°C.) |
|---|---|---|---|---|---|
| IV-13 | 3,4-dichlorophenyl (Cl, Cl) | H | — | cis | 149–151 |
| IV-14 | 4-chlorophenyl (Cl) | H | — | cis | 142–144 |
| IV-15 | 2,6-dichlorophenyl (Cl, Cl) | t-C₄H₉ | — | trans | 190–192 |
| IV-16 | 2-F, 6-Cl phenyl | Cl | — | cis | 206–208 |
| IV-17 | 2,6-difluorophenyl (F, F) | Cl | — | cis | 164 |
| IV-18 | 2,6-dichlorophenyl (Cl, Cl) | Cl | 2-Cl | cis | 215–218 |

EXAMPLE VI-1

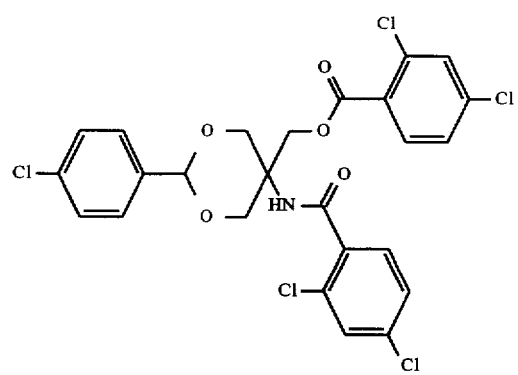

5 ml of triethylamine are added to 4.1 g (15 mmol) of 2-(4-chlorophenyl)-5-amino-5-hydroxymethyl-1,3-dioxane in 100 ml of methylene chloride, and 6.3 g (30 mmol) of 2,4-dichlorobenzoyl chloride in 5 ml of methylene chloride are added dropwise at 0° C. The reaction mixture is stirred for 15 hours at room temperature and washed with water, the organic phase is dried using magnesium sulfate and concentrated in vacuo, and the residue is precipitated by digestion with n-hexane. 8.3 g (approximately 94% of theory) of the compound shown above of melting point 148°–150° C. are obtained.

The compounds listed in Table 11 are obtained analogously to Example (VI-1)

TABLE 11

Structure (VI): Ar¹-C(O)-O-CH₂-C(NH-C(O)-Ar¹)(CH₂-O-)... dioxane ring with Ar bearing R¹ and R²ₘ

| Ex. No. | Ar¹ | R¹ | R²ₘ | M.p. °C. |
|---|---|---|---|---|
| VI-2 | 2-F, 6-Cl phenyl | H | H | 162–164 |
| VI-3 | 2-F, 6-F phenyl | C₄H₉-t | H | 182–184 |
| VI-4 | 2-Cl phenyl | H | H | 124–126 |

TABLE 11-continued (VI) structure: Ar¹-C(=O)-O-CH₂-C(NH-C(=O)-Ar¹)(CH₂-O-)(CH₂-O-)CH-Ar(R²m)(R¹) [1,3-dioxane with Ar¹CONH and Ar¹COOCH₂ substituents]

| Ex. No. | Ar¹ | R¹ | R²m | M.p. °C. |
|---|---|---|---|---|
| VI-5 | 2-F, 6-Cl-phenyl | C₄H₉-t | H | 188–190 |
| VI-6 | 2-F-phenyl | H | H | 134–136 |
| VI-7 | 2-F, 6-Cl-phenyl | Cl | H | 168–170 |
| VI-8 | 2,6-di-F-phenyl | Cl | H | 164 |
| VI-9 | 2,6-di-Cl-phenyl | Cl | H | 176–178 |
| VI-10 | 2,4-di-Cl-phenyl | Cl | H | 148–150 |
| VI-11 | 2,6-di-Cl-phenyl | Cl | H | 124–126 |
| VI-12 | 4-Cl-phenyl | Cl | H | 170–172 |
| VI-13 | 2-F, 6-Cl-phenyl | Cl | 2-Cl | 186–187 |
| VI-14 | 2,6-di-F-phenyl | Cl | 2-Cl | 202–204 |
| VI-15 | 2,4-di-Cl-phenyl | Cl | 2-Cl | 184–185 |
| VI-16 | 2,6-di-Cl-phenyl | Cl | 2-Cl | 161–162 |
| VI-17 | 4-Cl-phenyl | Cl | 2-Cl | 181–183 |

Starting substances of the formula (VII)

EXAMPLE (VII-1)

(VI)

81 g (0.5 mol) of 4-t-butyl-benzaldehyde are introduced into 500 ml of toluene, 5 g of p-toluene-sulfonic acid are added, 76 g (0.5 mol) of tris-hydroxymethylnitromethane are added, and the mixture is heated on a water separator until water separation has ceased. The reaction mixture is then washed using 5% strength sodium hydrogen carbonate solution and subsequently concentrated. The residue is recrystallized from toluene/cyclohexane.

116 g (78% of theory) of 2-(4-t-butyl-phenyl)-5-hydroxymethyl-5-nitro-1,3-dioxane of melting point 90° C.–92° C. are obtained.

The compounds of the formula (VII) listed in Table 12 were obtained analogously to Example (VII-1):

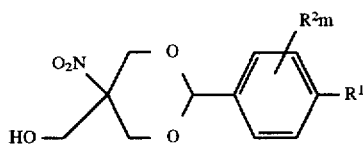

TABLE 12

| Ex. No. | R¹ | R²ₘ | Isomer | M.p. °C. |
|---|---|---|---|---|
| VII-2 | C₄H₉-t | — | trans | 143–145 |
| VII-3 | Cl | 2-Cl | Cis | 141–142 |

Use Examples

Example A

Tetranychus test (OP resistant-immersion treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentrations.

Bean plants (Phaseolus vulgaris) which are severely infested with all development stages of the greenhouse red spider mite (Tetranychus urticae) are immersed in a preparation of active compound of the desired concentration.

After the desired period of time, the activity in % is determined. 100% means that all the spider mites have been killed; 0% means that none of the spider mites have been killed.

In this test, a degree of destruction of 98% is shown, after 7 days, for example by the compounds of Preparation Examples I-9 and I-11 at an active compound concentration of 0.01% and I-16 at 0.02%.

Example B

*Phaedon larvae* test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with mustard beetle larvae (Phaedon cochleariae) while the leaves are still moist.

After the desired period of time, the destruction in % is determined. 100% means that all the beetle larvae have been killed; 0% means that none of the beetle larvae have been killed.

In this test, a degree of destruction of 100% is shown, after 7 days, for example by the compound of Preparation Example I-10 at an exemplary active compound concentration of 0.1%.

Example C

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the diamond-back moth (Plutella maculipennis) while the leaves are still moist.

After the desired period of time, the destruction in % is determined. 100% means that all the caterpillars have been killed; 0% means that none of the caterpillars have been killed.

In this test, a degree of destruction of 100% was shown, after 7 days, for example by the compound of Preparation Example I- 2 at an exemplary active compound concentration of 0.1%.

Example D

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of active compound of the desired concentration and are infested with caterpillars of the fall army worm (Spodoptera frugiperda) while the leaves are still moist.

After the desired period of time, the destruction in % is determined. 100% means that all the caterpillars have been killed; 0% means that none of the caterpillars have been killed.

In this test, a degree of destruction of 100% was shown, after 7 days, for example by the compound of Preparation Example I-11 at an exemplary active compound concentration of 0.1%.

We claim:

1. An Azatrioxaspiroalkene of the formula (I)

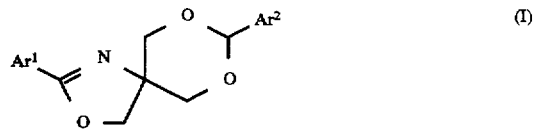

in which

Ar¹ represents phenyl which maybe monosubstituted to disubstituted by identical or different substituents selected from the group consisting of fluorine, chlorine, bromine, hydroxyl, methyl, ethyl, n- or i-propyl, methoxy, ethoxy, n- or i-propoxy, trifluoromethyl or trifluoromethoxy, and Ar² represents phenyl which may be monosubstituted to trisubstituted by identical or different substituents selected from the group consisting of fluorine, chlorine, bromine, cyano, nitro, hydroxyl, or methyl, ethyl, n- or i-propyl, n-, i-, s- or t-butyl, n-, i-, s- or t-pentyl, n-, i-, s- or t-hexyl, n- or i-octyl, n- or i-nonyl, n- or i-decyl, n- or i-dodecyl, methoxy, ethoxy, n- or i-propoxy, n-, i-, s- or t-butoxy, n-, i-, s- or t-pentyloxy, n-, i-, s- or t-hexyloxy, n- or i-octyloxy, n- or i-nonyloxy, n- or i-decyloxy, n- or i-dodecyloxy, methylthio, ethylthio, n- or i-propylthio, n-, i-, s- or t-butylthio, n-, i-, s- or t-pentylthio, n-, i-, s- or t-hexylthio, n- or i-octylthio, n- or i-nonylthio, n- or i-decylthio, n- or i-dodecylthio, acetyl, propionyl, n- or i-butyroyl, n-, i-, s- or t-valeroyl, methoxycarbonyl, ethoxycarbonyl, n- or i-propoxycarbonyl, n-, i-, s- or t-butoxycarbonyl, n-, i-, s- or t-pentoxycarbonyl, methylenedioxy, ethylenedioxy, each of which maybe substituted by fluorine or chlorine, or cyclohexyl, cyclohexylmethyl or cyclohexyloxy, each of which maybe substituted by methyl, ethyl, n- or i-propyl, n-, i-, s- or t-butyl, methoxy, ethoxy, n- or i-propoxy, n-, i-, s- or t-butoxy, cyclohexyl or phenyl.

2. A composition for killing insects, acarides and nematodes which comprises at least one compound of the formula (i) as claimed in claim 1.

3. A method of killing insects, acarides and nematodes as claimed in claim 1 wherein compounds of the formula (I) as claimed in claim 1 are allowed to act on animal pests or their environment.

* * * * *